United States Patent
Stenkamp

(10) Patent No.: US 6,462,350 B1
(45) Date of Patent: Oct. 8, 2002

(54) LIGHT SOURCE, OPTICAL WINDOW, AND DETECTOR CONFIGURATION FOR MEASUREMENT OF A MEDIUM

(75) Inventor: Bernd Stenkamp, Stuttgart (DE)

(73) Assignee: Endress + Hauser Conducta Gesellschaft für Mess- und Regeltechnik mbH + Co., Gerlingen (DE)

( * ) Notice: Subject to any disclaimer, the term of this patent is extended or adjusted under 35 U.S.C. 154(b) by 0 days.

(21) Appl. No.: 09/497,108

(22) Filed: Feb. 3, 2000

(30) Foreign Application Priority Data

Feb. 6, 1999 (DE) .......................................... 199 04 880

(51) Int. Cl.$^7$ .............................................. G01N 15/06
(52) U.S. Cl. ...................................... 250/573; 356/446
(58) Field of Search ................................ 250/573, 574; 356/342, 343, 441, 442, 446

(56) References Cited

U.S. PATENT DOCUMENTS

| | | | | |
|---|---|---|---|---|
| 4,365,896 A | * | 12/1982 | Mihalow | 356/446 |
| 5,039,225 A | * | 8/1991 | Uekusa | 356/448 |
| 5,703,568 A | * | 12/1997 | Hegyi | 340/602 |

FOREIGN PATENT DOCUMENTS

| EP | 0 634 645 | 1/1995 |
|---|---|---|
| JP | 58 187 836 | 2/1983 |

* cited by examiner

*Primary Examiner*—Stephone Allen
(74) *Attorney, Agent, or Firm*—Paul Vincent

(57) ABSTRACT

The invention concerns an opto-electronic sensor, in particular for the measurement of opaqueness in a medium, having a transmitter channel (6) irradiating light waves along a first axis (20) and with at least one receiver channel (8, 10) which detects light waves interacting with the medium and which cooperates within an evaluation unit. In order to optically isolate the transmitter and receiver channels from each other, the sensor is configured in such a fashion that a common window (12) made from an optically transparent material is provided for sealing the transmitter channel (6) and the receiver channel (8, 10) with respect to the medium to be measured and for coupling in and coupling out the light waves. The inner border surface (16) of the window (12) facing the receiver channel (8, 10) is adjacent to an optically thinner medium and is oriented relative to the outer border surface (14) of the window (12) directly adjacent to the medium to be measured and with respect to the orientation of the first axis (20) relative to this outer border surface (14), in such a manner that light waves (D-TR) from the transmitter channel (6) which are reflected back into the window (12) from the outer border surface (14) are incident upon the inner border surface (16) at an angle of incidence ($\alpha_2$) which is larger than the critical angle for total internal reflection so that they do not enter into the receiver channel (8, 10), but are once more reflected.

11 Claims, 2 Drawing Sheets

LIGHT SOURCE, OPTICAL WINDOW, AND DETECTOR CONFIGURATION FOR MEASUREMENT OF A MEDIUM

This application claims Paris Convention priority of DE 199 04 880.0 filed Feb. 6, 1999 the complete disclosure of which is hereby incorporated by reference.

BACKGROUND OF THE INVENTION

The invention concerns an opto-electronic sensor, preferentially for measuring the opaqueness of a medium, having a transmitter channel for transmitting light waves along a first axis and at least one receiver channel for detecting light waves which have interacted with the medium, wherein the receiver channel cooperates with an evaluation unit. The invention also concerns a method for operating an opto-electronic sensor.

Sensors of this type are used to measure the properties of fluids, in particular, in the food and chemical industry and are often used for continuous measurements in processing technology. The above mentioned applications have stringent requirements for the temperature stability and the resistive strength to pressure as well as the stability with regard to aggressive chemicals. These requirements result, i.e. from the need to clean and sterilize sensors used in these food and chemical industries.

Opto-electronic sensors have the inherent problem of requiring optical isolation between the transmitter and receiver channels. Transmitter channel light waves are modulated for identification purposes to facilitate detection by the evaluation unit. Under all circumstances, light waves must be prevented from leaving the transmitter channel and gaining direct access to the receiver channel without having interacted with the medium, since this would falsify or prohibit measurement thereof.

This can be achieved when the transmitter channel and the receiver channel each have their own housing. However, this complicates the sensor and results in increased difficulty and expense. Alternatively, one can dispose both the transmitter channel and the receiver channel within one housing and separate them from each other using optically opaque materials. Although this is relatively easy to do inside of the sensor housing, there are problems at the interface or exit location into the medium to be measured. Two separate windows made from one optically transparent material are required which increases the difficulty and expense of the seal.

Departing therefrom it is the underlying purpose of the present invention to improve an opto-electronic sensor of the above mentioned kind as well as a method for operation of a sensor of this type in such a fashion that the sensor is more compact and can be manufactured more economically to reduce the degree of difficulty and expense of optical isolation between the transmitter channel and the receiver channel and for sealing the sensor housing with respect to the medium to be measured.

SUMMARY OF THE INVENTION

This purpose is achieved in accordance with the invention with a sensor of the above mentioned kind in that a common window is used for sealing the transmitter channel and the receiver channel with respect to the medium to be measured as well as for coupling in and out the light waves, the window being made from an optically transparent material, wherein the inner border surface of the window facing the receiver channel is adjacent to an optically thinner medium having a lower optical index of refraction than that of the window material and is oriented in such a manner with respect to the outer border surface of the window adjacent to the medium to be measured as well as with respect to the orientation of the first axis relative to this outer border surface, that light waves from the transmitter channel which are reflected back from the outer border surface into the window are incident on the inner border surface at an angle which is larger than the critical angle for total internal reflection so that the light does not enter into the receiver channel, but is reflected again. In accordance with the invention, the incident angle for the transmitter light beam is chosen in such a fashion that light from the transmitter reflected from the outer border surface into the window is incident on the inner border surface at an angle which exceeds the total internal reflection angle.

The light is reflected and thereby does not enter into the receiver channel.

The additional purpose is solved with a method having the features of the independent method claim.

The solution in accordance with the invention facilitates use of one and the same exit location (the window) both for the transmitter channel and for one or a plurality of receiver channels without having to provide for optically opaque materials in the form of walls or the like between the receiver and transmitter channels. Irradiated light waves from the transmitter channel which did not enter into the measuring media but were reflected back at the border surface with the medium cannot enter into the receiver channel. These light waves are totally internally reflected at the inner surface of the window facing the inside of the sensor, proximate the transmitter channel. This is facilitated by providing for an optically thinner material (preferentially air or another gas) at this inner border surface, i.e. inside the sensor. Light waves incident on this inner border surface at an angle of incidence in excess of the critical angle for total internal reflection are once more reflected into the window towards the outer border surface. It has turned out to be particularly advantageous when the window comprises a plane-parallel plate since, in this case, the back reflected portion is incident on the outer border surface at the same angle as the primary transmitter beam so that most of it exits. The portion which is once more reflected towards the inner border surface does however pass into the sensor, since the light waves are once more incident on the lower border surface at an angle which exceeds the critical angle for total internal reflection.

Light waves which, after interacting with the medium to be measured (e.g. through scattering with non-dissolved particles in a liquid), are incident from the outside onto the outer border surface of the window and enter into the optically transparent window material, then pass through the inner border surface into the sensor when they are incident at an angle which is less than the critical angle for total internal reflection. One orients the transmitter channel and thereby the first axis along which the light waves propagate within the window in such a fashion that the light is preferentially incident on the outer border surface at an angle between 45° and 55° relative to the normal. In this case, the so-called 90° scattered light is incident on the inner border surface at an angle which is less than the critical angle for total internal reflection (assuming a watery measuring medium, an optically transparent window material made from glass as well as an optically thinner medium in the form of air inside the window).

It has also turned out to be advantageous when the first axis is oriented relative to the outer border surface in such a fashion that the angle $\alpha_2$, at which those light waves reflected back from the outer border surface into the window are incident upon the inner border surface, is larger than 42°. It has furthermore turned out to be advantageous when the angle of incidence $\alpha_3$, at which light waves which pass into the window due to interaction with the medium to be measured are incident on the inner border surface, is less than 40°, preferentially less than 34°.

Further features, details and advantages of the invention can be extracted from the accompanying claims and from the drawings as well as from the following description of a preferred embodiment of the sensor in accordance with the invention.

DESCRIPTION OF THE PREFERRED EMBODIMENT

Figure 1:
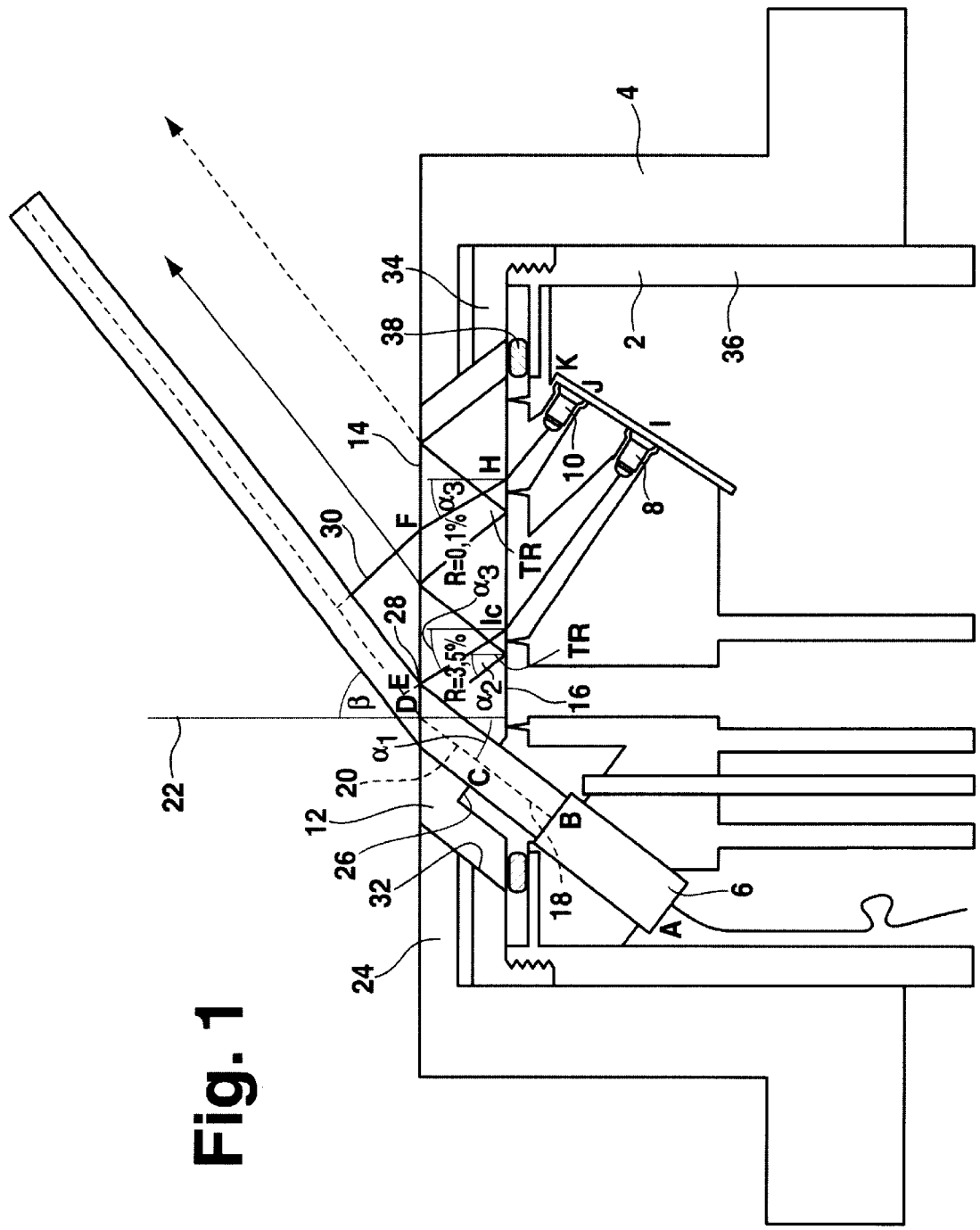
FIG. 1 shows a schematic section of a sensor for opaqueness measurements in accordance with the invention and FIG. 2 plots the optical reflectivity at a border surface between glass/air and sapphire/air in dependence on the angle of incidence.

FIG. 1 schematically shows an opto-electronic sensor. The sensor comprises a sensor housing 2 which can be inserted into a mounting flange 4, in turn, which can be inserted and mounted within an opening in a container filled with liquid and submerged therein, for use e.g. in processing measuring technology. The opto-electronic sensor is an opaqueness sensor and measures light diffusely scattered from non-dissolved particles in a liquid, gas, or an emulsion. Towards this end, a beam of light is introduced into the medium to be measured and the scattered light is opto-electronically detected.

The sensor comprises a transmitter channel 6 and two receiver channels 8, 10 which are accommodated in a common sensor housing 2 and are sealed-off from the medium to be measured via a common window 12 made from an optically transparent material. The light waves transmitted from the transmitter channel pass outwardly into the medium to be measured through the same window as the light scattered by scattering centers of the medium to be measured and passing from the outside through the window in an inward direction to the receiver channels 8, 10. Optical isolation between the outgoing transmitter light waves and the light waves to be received is effected by means of the geometrical configuration or orientation of the outer and inner border surfaces 14 and 16 of the window 12 and by the orientation of the light waves irradiated from the transmitter channel 6 in propagation direction 18 relative to the outer border surface 14, as described below.

The transmitter channel 6, having the one light source, is oriented in such a fashion that it transmits light onto the outer border surface 14 of the window in the device wall 24 in a vertical plane at an angle $\alpha_1$ of approximately 45° relative to the normal. These light waves are incident on a section 26 of the window which is shaped in such a fashion that it is precisely perpendicular to the propagation direction 18 of the light waves. They therefore pass, without change of direction, along a first axis 20, into the window 12 and impinge on the outer border surface 14 of the window 12 at an angle of incidence $\alpha_1$, and pass into the medium to be measured. The light waves therefore subtend the path B-C-D without change of direction. At the border surface 14, the light waves are refracted away from the normal 22 at the transition into the measuring medium (e.g. a watery solution) and exit out of the window 12 and into the medium to be measured at an angle $\beta$ which is larger than the incident angle $\alpha_1$. As suggested in FIG. 1, approximately 96.5% of the intensity enters into the medium to be measured (for a transition between glass, n=1.52 and water n=1.33, at an angle of incidence of $\alpha_1$=45°). The remaining 3.5% is reflected back towards the sensor 12 at the border surface 14 (D-TR). The geometry of the inner border surface 16 and the outer border surface 14 and the orientation of the first axis 20 are chosen in such a fashion that light waves reflected back into the window 12 (D-TR) are incident on the inner border surface 16 at an angle $\alpha_2$ which is larger than the critical angle for total internal reflection at the transition between glass to the bordering, optically thinner material, namely air. As a result thereof, the light waves are once more reflected back at the border surface 16 into of the window 12. When they impinge once more on the outer border surface 14, a substantial fraction passes into the medium to be measured (3.4% for a transition glass/water). The remaining 0.1% of the original intensity is however reflected inwardly. One thereby guarantees that the light waves irradiated by the transmitter channel 6 do not enter into the receiver channel 8 or 10 without requiring separate housings or separate windows for the transmitter and receiver channels and undesirable and troublesome optical shielding means.

FIG. 1 also shows the "90°" scattered light in the form of "beams" 28, 30. These "beams" are incident on the outer border surface 14 at points E and F respectively and most of the light associated therewith enters into the optically transparent material of the window 12. Since this material is the optically denser medium, the light waves are refracted in the direction towards the normal (E-G and F-H respectively). The orientation of the outer border surface 14 and the inner border surface 16 as well as the orientation of the first axis 20 of the light waves radiated from the transmitter channel 6 is chosen in such a fashion that this 90° scattered light is incident on the inner border surface 16 at an angle $\alpha_3$ which is preferentially significantly smaller than the critical angle for total internal reflection at the interface between the optically transparent material of the window 12 and the bordering optically thinner medium i.e. air. The smaller the angle $\alpha_3$, the higher the intensity of light waves passing through the window 12 into the bordering air which then reach the receiver channels 8 and 10 respectively for detection (G-I and H-J).

In this manner, an effective optical separation between the transmitter channel 6 and the receiver channels 8 and 10 is achieved.

As can be seen in FIG. 1, the window 12 is inserted into a conical opening 32 of an inner housing flange 34 which can be screwed, via an inner thread, onto an outer threaded section of a cylindrical inner housing component 36. The window itself has the shape of a truncated cone with plane-parallel border surfaces 14, 16. Screwing of the flange 34 onto the inner housing portion 36 presses the window 12 against a seal 38. The unit made in this fashion is sealed into the mounting flange 4 in such a manner that the outer border surface 14 of the window 12 is flush with the outer flange end portion 24.

Figure 2:
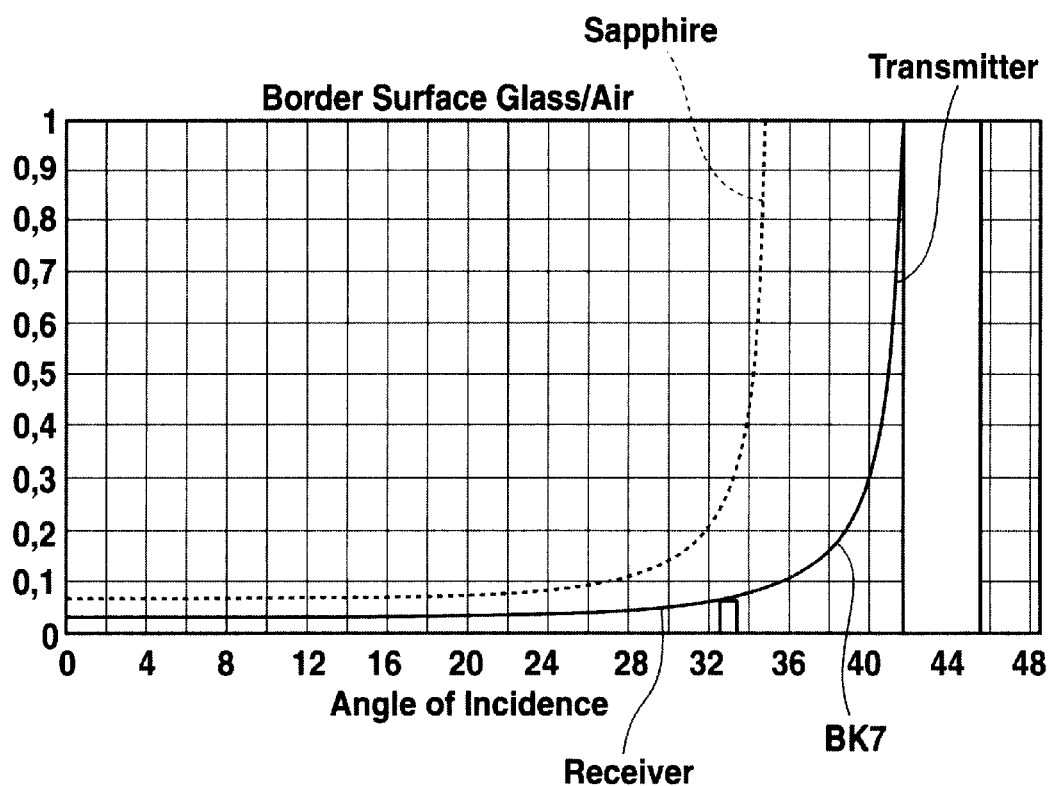

FIG. 2 shows the reflectivity in dependence on the incident angle for two optically transparent materials, sapphire and BK7 glass.

An incident angle region above 41.7° relative to the normal 22 is indicated for the transmitter beam and the first axis 20 along which the transmitter channel light waves propagate in the window 12 towards the outer border surface 14. Within this range, one can be sure that the light waves irradiated from the transmitter channel 6 substantially pass into the medium to be measured. In addition, no light reflected from the transition at the outer border surface 14 can escape in an inward direction at the inner border surface 16 (glass/air), since the critical angle for total internal reflection is exceeded. The additional preferred angular region indicated in FIG. 2 about 33° is associated with the scattered light. This region lies below the critical angle for total internal reflection (even for sapphire) at the transition for the light waves on the border surface sapphire/air.

Clearly, the configuration described above, having plane parallel border surfaces 14, 16, is not the only configuration in accordance with the invention with which the described optical isolation (without use of a separating member) between the transmitter and the receiver channel can be realized. It would also be possible to use different configurations, e.g. a wedge-shaped configuration or another suitable window 12 to guarantee that light waves directly transmitted from the transmitter channel 6 cannot escape out of the window material in the inward direction to enter into the receiver channels 8, 10, with the scattered light which is to be measured or detected being passed back into the sensor after interacting with the media to be measured and enters into the receiver channels 8, 10.

I claim:

1. An opto-electronic sensor for measurement of a first medium, the first medium having a first index of refraction, the measurement being effected by detection means disposed in a second medium having a second index of refraction, the sensor comprising:

a window made from an optically transparent material having a third index of refraction greater than the second index of refraction, said window disposed between the first medium and the second medium for sealing the first medium with respect to the second medium, said window having a first surface adjacent to said first medium and a second surface adjacent to said second medium;

a transmitter channel for irradiating first light along a first axis to pass through said window and into the first medium through said first surface;

at least one receiver channel disposed in said second medium, said receiver channel detecting second light originate from interactions between said first light and the first medium, said second light passing through said window and into said receiver channel; and an evaluation unit connected to said receiver channel for processing information from said receiver channel, wherein said first surface, said second surface and said first axis are oriented such that third light originating from reflection of said first light on said first surface is incident on said second surface at an angle which exceeds a critical angle for internal reflection at said second surface, whereby said third light is reflected from said second surface back into said window and does not enter into said receiver channel.

2. The sensor of claim 1, wherein said first axis is oriented relative to said first surface in such a fashion that said first light is incident on said first surface at a first angle between 45° and 55° relative to a normal.

3. The sensor of claim 1, wherein said first axis is oriented relative to said first surface in such a fashion that said third light impinges on said second surface at a second angle larger than 42°.

4. The sensor of claim 1, wherein said second light is incident on said second surface, at a third angle less then 40°.

5. The sensor of claim 4, wherein said third angle is less than 34°.

6. The sensor of claim 1, wherein the second medium is a gas.

7. The sensor of claim 6, wherein said gas is air.

8. The sensor of claim 1, wherein said window is made from a glass material.

9. The sensor of claim 1, wherein said window comprises a plane parallel plate made from an optically transparent material.

10. The sensor of claim 1, wherein said second light is 90° scattered light.

11. Method for operating an opto-electronic sensor for measurement of a first medium, the method comprising the steps of;

a) separating said first medium from a second medium by means of an optically transparent window, said window having an index of refraction, a first surface adjacent to said first medium, and a second surface adjacent to said second medium;

b) irradiating first light towards said window along an incident light axis to initially pass through said second surface into said window and through said first surface into the first medium, said first medium generating second light in response to irradiation from said first light, a fraction of said first light not passing from said window through said first surface but reflecting from an inner side of said first surface to generate third light within said window;

c) positioning a detector in said second medium to detect said second light; and d) orienting said first surface, said second surface and said incident light axis and selecting said index of refraction such that said third light is incident on said second surface at an angle which exceeds a critical angle for total internal reflection between said window and said second medium and such that said second light is incident on said second surface through said window at an angle which is less than said critical angle.

* * * * *